United States Patent
Xu et al.

(10) Patent No.: US 12,050,220 B2
(45) Date of Patent: Jul. 30, 2024

(54) CELL LABELING AGENT AND CELL LABELING KIT

(71) Applicant: University of Miyazaki, Miyazaki (JP)

(72) Inventors: Yan Xu, Miyazaki (JP); Takumi Ishizuka, Miyazaki (JP); Pei-Yan Zhao, Miyazaki (JP)

(73) Assignee: University of Miyazaki, Miyazaki (JP)

( * ) Notice: Subject to any disclaimer, the term of this patent is extended or adjusted under 35 U.S.C. 154(b) by 1031 days.

(21) Appl. No.: 16/967,306

(22) PCT Filed: Jan. 25, 2019

(86) PCT No.: PCT/JP2019/002440
§ 371 (c)(1),
(2) Date: Aug. 4, 2020

(87) PCT Pub. No.: WO2019/151128
PCT Pub. Date: Aug. 8, 2019

(65) Prior Publication Data
US 2021/0033617 A1 Feb. 4, 2021

(30) Foreign Application Priority Data

Feb. 5, 2018 (JP) .................. 2018-018172

(51) Int. Cl.
*C07H 13/12* (2006.01)
*G01N 33/58* (2006.01)

(52) U.S. Cl.
CPC ........... *G01N 33/582* (2013.01); *C07H 13/12* (2013.01)

(58) Field of Classification Search
None
See application file for complete search history.

(56) References Cited

U.S. PATENT DOCUMENTS

2008/0075661 A1  3/2008  Robillard et al.
2010/0297250 A1  11/2010 Boons et al.
2013/0137763 A1  5/2013  van Delft et al.
2013/0344527 A1  12/2013 Bertozzi et al.
2016/0166704 A1  6/2016  Adamo et al.
2017/0002012 A1  1/2017  Van Delft et al.

FOREIGN PATENT DOCUMENTS

JP    2008-515875 A    5/2008
JP    2011-504507 A    2/2011
JP    2013-525425 A    6/2013
JP    2016-506905 A    3/2016
JP    2017-505770 A    2/2017
WO    2019/151128 A1   8/2019

OTHER PUBLICATIONS

Agarwal et al., Angewandte Chemie, International Edition, 2015, vol. 54(39), pp. 11504-11510 . (Year: 2015).*
Chang et al., Metabolic labeling of sialic acids in living animals with alkynyl sugars. Angew Chem Int Ed Engl., 48(22):4030-4033 (2009).
Agarwal et al., Systemic fluorescence imaging of Zebrafish glycans with Bioorthogonal Chemistry. Angew. Chem. Int. Ed., 54:11504-11510 (2015).
Bateman et al., N-propargyloxycarbamate monosaccharides as metabolic chemical reporters of carbohydrate salvage pathways and protein glycosylation. Chem. Commun., 49:4328-4330 (2013).
Ning et al., Visualizing metabolically labeled glycoconjugates of living cells by copper-free and fast huisgen cycloadditions. Angew. Chem. Int. Ed., 47:2253-2255 (2008).
Agard et al., A strain-promoted [3+2] azide-alkyne cycloaddition for covalent modification of biomolecules in living systems. J. Am. Chem. Soc., 126:15046-15047 (2004).
International Search Report and Written Opinion, mailed May 7, 2019, for International Application No. PCT/JP2019/002440 filed on Jan. 25, 2019.

* cited by examiner

*Primary Examiner* — Traviss C McIntosh, III
(74) *Attorney, Agent, or Firm* — K&L Gates LLP; Louis C. Cullman; Giorgios N. Kefallinos

(57) ABSTRACT

The cell labeling agent includes a monosaccharide derivatives with a six-membered ring structure that are metabolized to sialic acid in the sialic acid biosynthetic pathway of cells. Among the groups bonded to carbon atoms constituting a six-membered ring in the monosaccharide derivatives, at least one group that does not change, even when metabolized by the sialic acid biosynthetic pathway, includes a ring structure with a carbon-carbon double bond or triple bond.

15 Claims, 5 Drawing Sheets

CELL LABELING AGENT AND CELL LABELING KIT

RELATED APPLICATIONS

This application is a national stage entry under 35 U.S.C. 371 of International Patent Application No. PCT/JP2019/002440, filed on Jan. 25, 2019, which claims priority to Japanese Patent Application No. 2018-018172 filed on Feb. 5, 2018, the entire content of each of which is incorporated herein by reference.

TECHNICAL FIELD

The present disclosure relates to a cell labeling agent and a cell labeling kit.

BACKGROUND ART

Metabolic labeling methods are known to use the metabolism of monosaccharides by the sialic acid biosynthetic pathway to label sugar chains on the cell surface. In the metabolic labeling method, for example, a derivative of N-acetyl mannosamine (ManNAc) with an azide group (peracetylated N-azidoacetyl mannosamine, Ac$_4$ManNAz) is used. Ac$_4$ManNAz taken up into the cell is enzymatically deacetylated in the cytoplasm and is metabolized to the corresponding N-azidoacetylsialic acid (SiaNAz). SiaNAz is incorporated into the sialo sugar complex and then is presented to the cell surface along with the sugar chains. A reporter substance with fluorescent dye can be reacted to the azido group of SiaNAz by a click reaction such as an azide-alkyne cycloaddition reaction (CuAAC) using a copper catalyst.

A metabolic labeling method using peracetylated N-(4-pentinoyl)mannosamine (Ac$_4$ManNAl) is disclosed in non-patent literature 1. Ac$_4$ManNAl is metabolized to the corresponding sialic acid (SiaNAl) in cells and is presented to the cell surface. Since SiaNAl has an alkyne at the end, the reporter substance can be added to the sugar chains on the cell surface by reacting the alkyne with azide in CuAAC.

CITATION LIST

Non Patent Literature

Non Patent Literature 1: Pamela V. Chang, Xing Chen, Chris Smyrniotis, Alexander Xenakis, Tianshun Hu, Carolyn R. Bertozzi, Peng Wu "Metabolic Labeling of Sialic Acids in Living Animals with Alkynyl Sugars" Angew. Chem. Int. Ed. 2009, 48, 4030-4033.

SUMMARY OF INVENTION

Technical Problem

In Ac$_4$ManNAz and Ac$_4$ManNAl, CuAAC must be used to add a reporter substance to a sugar chain via the azide or alkyne by sialic acid displayed on the cell surface. Because copper is toxic to living organisms, the addition of reporter substances in vivo using Ac$_4$ManNAz or Ac$_4$ManNAl is not safe. Therefore, it is difficult to apply Ac$_4$ManNAz and Ac$_4$ManNAl to clinical practice.

In view of the above circumstances, the present disclosure is intended to provide a cell labeling agent and a cell labeling kit which are safe and can be applied to clinical use.

Solution to Problem

A cell labeling agent according to a first aspect of the present disclosure includes monosaccharide derivatives with a six-membered ring structure that are metabolized to sialic acid in the sialic acid biosynthetic pathway of cells, wherein at least one group in the monosaccharide derivatives that does not change even when metabolized by the sialic acid biosynthetic pathway, includes a ring structure with a carbon-carbon double bond or triple bond among the groups bonded to carbon atoms constituting a six-membered ring in the monosaccharide derivatives In this case, the monosaccharide derivatives described above may be represented by the Formula (I), where R is the group containing the ring structure.

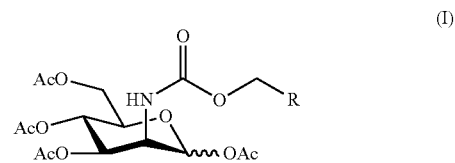

(I)

In addition, the monosaccharide derivatives described above may also be represented by the Formula (II), where R is the group containing the ring structure.

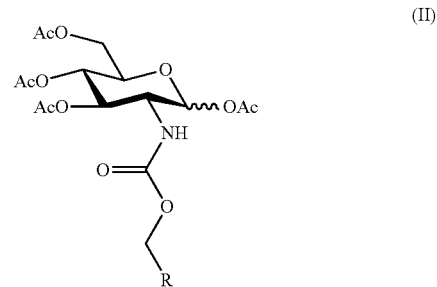

(II)

Furthermore, the monosaccharide derivatives described above may also be represented by Formula (III), where R is the group containing the ring structure.

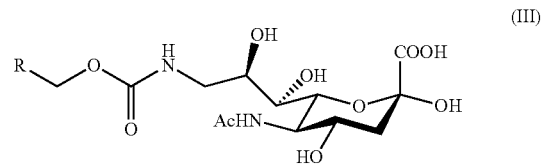

(III)

The group R may be selected from the group consisting of (a) to (m) below.

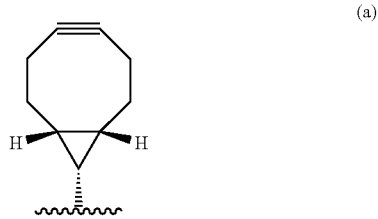

(a)

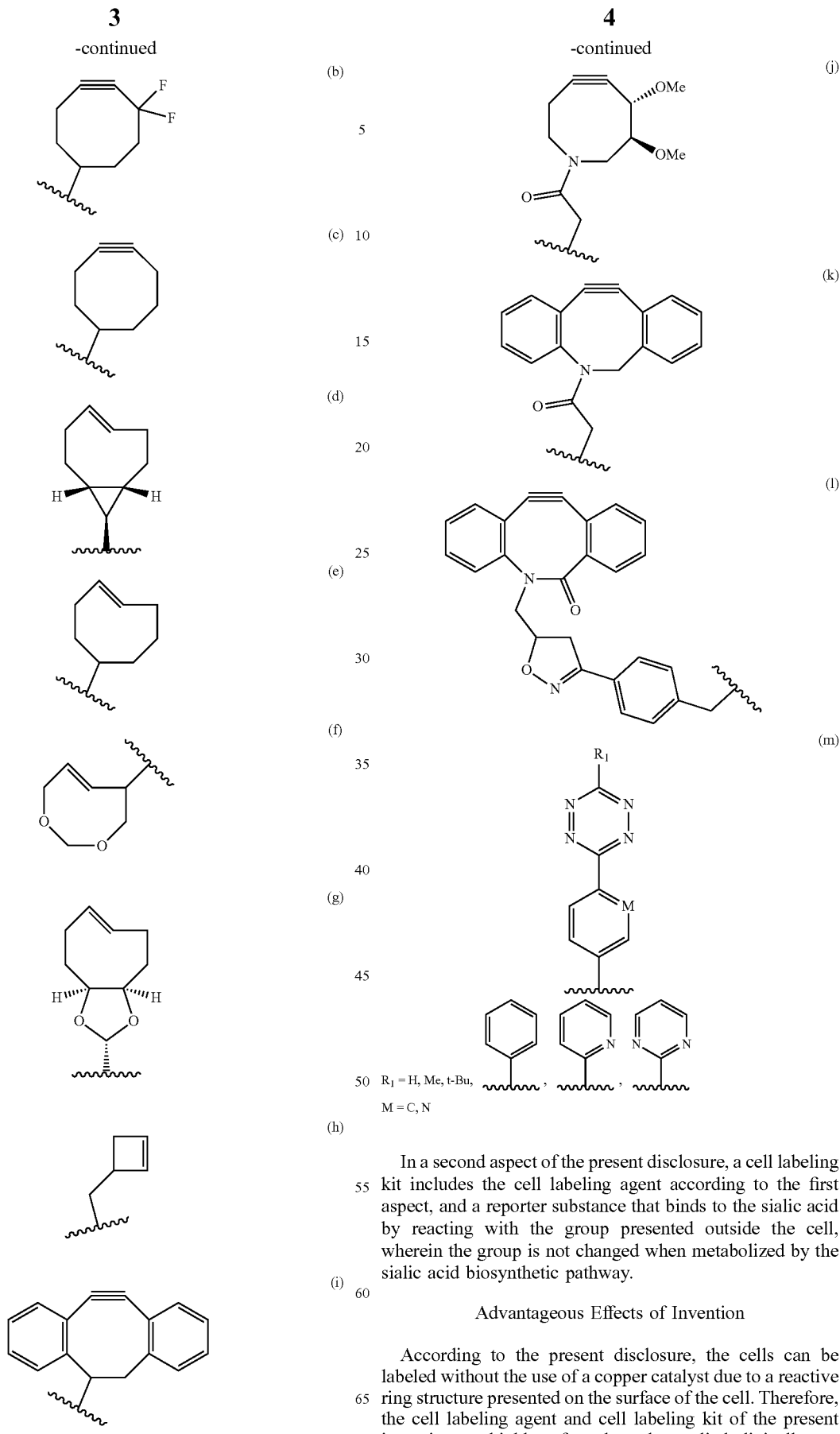

In a second aspect of the present disclosure, a cell labeling kit includes the cell labeling agent according to the first aspect, and a reporter substance that binds to the sialic acid by reacting with the group presented outside the cell, wherein the group is not changed when metabolized by the sialic acid biosynthetic pathway.

Advantageous Effects of Invention

According to the present disclosure, the cells can be labeled without the use of a copper catalyst due to a reactive ring structure presented on the surface of the cell. Therefore, the cell labeling agent and cell labeling kit of the present invention are highly safe and can be applied clinically.

DESCRIPTION OF EMBODIMENTS

The present disclosure will be described with respect to particular embodiments and with reference to certain drawings but the present disclosure is not limited thereto but only by the claims. The drawings described are only schematic and are non-limiting.

The cell labeling agent of the present disclosure is a monosaccharide derivative that is metabolized to sialic acid in the sialic acid biosynthetic pathway of cells. The cell in the present invention is not particularly limited as long as it is a cell in which the sialic acid biosynthetic pathway functions. Preferably, the cell is an animal cell. The cell may be a cell collected from a living body, a primary culture cell or a cell line. They may be normal cells or cancer cells.

In the sialic acid biosynthetic pathway, monosaccharide derivatives such as ManNAc which is incorporated into cells, are metabolized to the corresponding sialic acid by various enzymes and converted to a sugar chain containing sialic acid. The monosaccharides metabolized to sialic acid by the sialic acid biosynthetic pathway are based on a six-membered ring structure. Therefore, the above monosaccharide derivatives have a six-membered ring structure. Sialic acid is a general term for derivatives of neuraminic acid, especially for the acyl derivatives of neuraminic acid.

Figure 1:
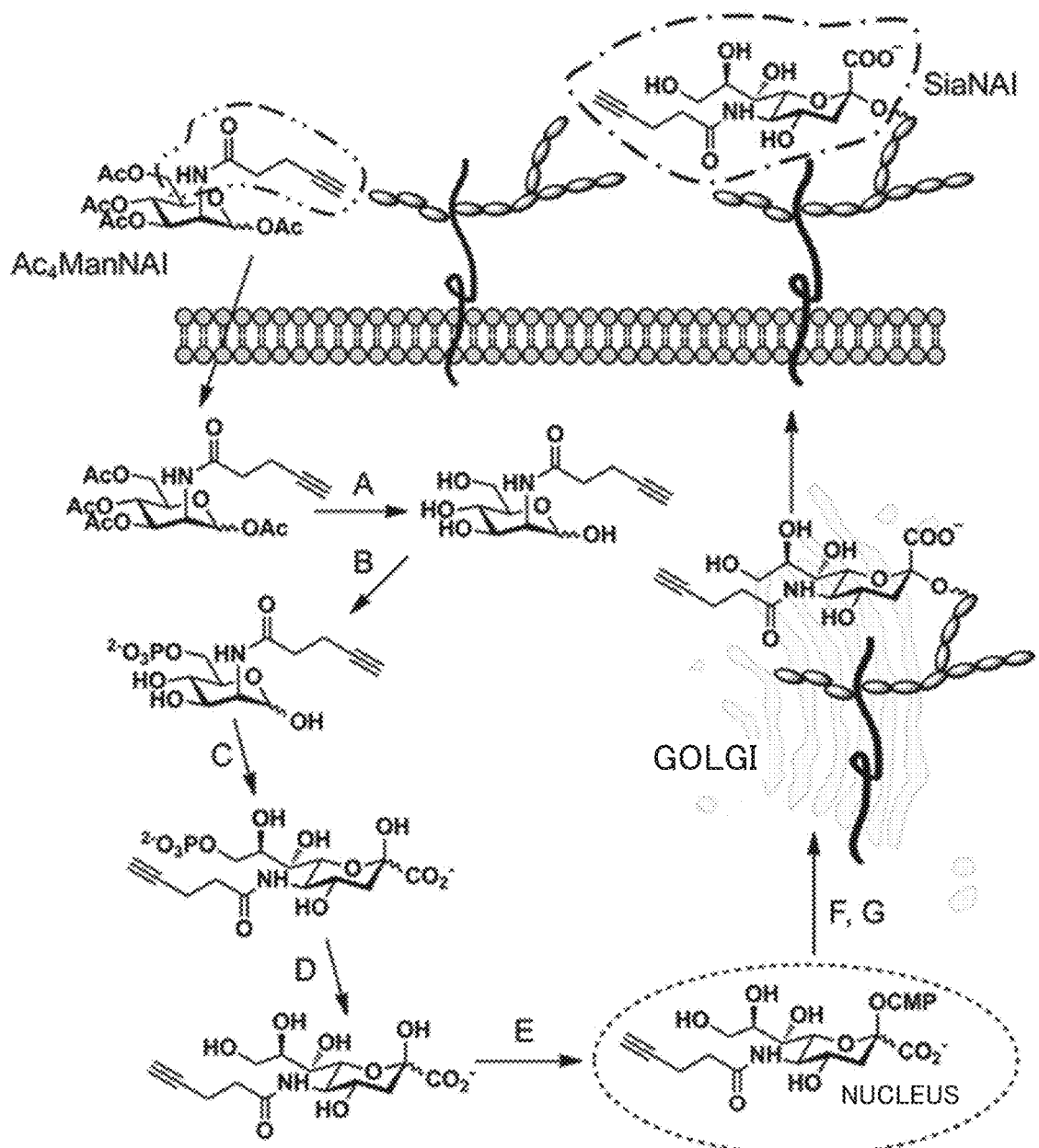
FIG. 1 shows the schematic diagram with a series of reactions in the sialic acid biosynthetic pathway.

FIG. 1 shows the sialic acid biosynthetic pathway in which $Ac_4ManNAl$ is metabolized by various enzymes and converted to a sugar chain containing SiaNAl (indicated by a single-dotted line). When $Ac_4ManNAl$ is taken up into the cell, it becomes CMP-sialic acid in the nucleus via the A-E reactions in the cytoplasm, and through the F and G reactions, SiaNAl-bound glycans are presented to the cell surface. The reactions of A, B, C, D, E, F and G are due to the action of non-specific esterase, ManNAc 6-kinase, sialic acid 9-phosphate synthase, sialic acid 9-phosphatase, CMP-sialic acid synthetase, CMP-sialic acid, Golgi transporter and sialic acid transferase, respectively.

Monosaccharide derivatives that are metabolized to sialic acid in the sialic acid biosynthetic pathway include, for examples, mannosamine derivatives, glucosamine derivatives, and sialic acid. The mannosamine derivative, the glucosamine derivative, and the sialic acid have at least one group that is not changed even if it is metabolized by the sialic acid biosynthetic pathway among the groups bonded to the carbon atoms constituting the six-membered ring. The term "group" as used herein means a group of atoms. Therefore, "group" does not include a hydrogen atom directly attached to a carbon atom comprising a six-membered ring.

Comparing the structure of $Ac_4ManNAl$ (as a mannosamine derivative) and SiaNAl generated by metabolism in FIG. 1, the group including amino group (highlighted by the double-dotted line) of $Ac_4ManNAl$ is maintained in SiaNAl. The group enclosed by the two-dotted line is attached to the carbon atom of the six-membered ring in the monosaccharide derivative that is not changed by metabolism in the sialic acid biosynthetic pathway for $Ac_4ManNAl$.

The monosaccharide derivatives in the present disclosure include a ring structure in which at least one group attached to a carbon atom comprising a six-membered ring in the monosaccharide derivative that does not change when metabolized by the sialic acid biosynthetic pathway. It has a carbon-to-carbon double bond or a triple bond.

When a mannosamine derivative is used as a monosaccharide derivative, the monosaccharide derivative is preferably represented by Formula (I), wherein R is the group containing a ring structure.

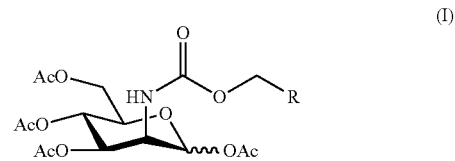

(I)

When a glucosamine derivative is used as a monosaccharide derivative, for example, a monosaccharide derivative represented by Formula (II) is preferred.

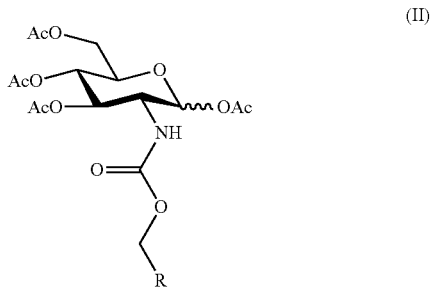

(II)

In the case of the mannosamine derivative represented by Formula (I) and the glucosamine derivative represented by Formula (II), among the groups bonded to the carbon atoms constituting the six-membered ring, a group of the monosaccharide derivative, that does not change even when metabolized to sialic acid in the sialic acid biosynthetic pathway, is the group containing an amino group bonded to the 2-position (—NH—C(=O)—O—C—R). R is included in the group bonded to the 2-position.

The structure of the sialic acid is exemplified by Formula (IV). In the sialic acid represented by Formula (IV), the groups attached to the carbon atoms comprising the six-membered ring that do not change when metabolized by the sialic acid biosynthetic pathway, are a carboxyl group attached to the 2-position (—COOH, including the carbon at the 1-position), a hydroxy group (—OH) attached to the 4-position, an acetylamide group (—NHAc) attached to the 5-position, and a group attached to the 6-position (—C(OH)—C(OH)—C(OH), including the carbons at the 7, 8, and 9 positions).

(IV)

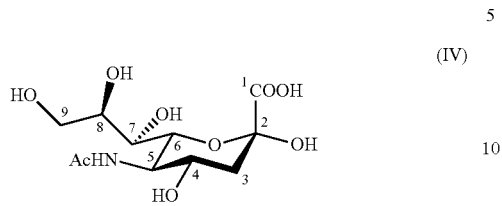

When sialic acid is used as a monosaccharide derivative, the monosaccharide derivative represented by Formula (III) is preferred.

(III)

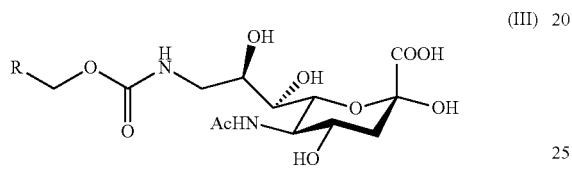

In the monosaccharide derivative represented by Formula (III), the groups attached to the carbon atoms comprising the six-membered ring that are not changed by metabolism in the sialic acid biosynthetic pathway, are a carboxyl group attached to the 2-position, a hydroxy group attached to the 4-position, an acetylamide group attached to the 5-position and a group (—C(OH)—C(OH)—C—NH—C(=O)—O—C—R) attached to the 6-position. R is contained in the group attached to the 6-position.

When the monosaccharide derivative is a sialic acid represented by Formula (III), the monosaccharide derivative is taken up into the cell and transported into the nucleus (E in FIG. 1). The monosaccharide derivative is then presented to the cell surface via the Golgi body, similar to Ac$_4$ManNAl.

The group R described above includes a variety of groups containing a ring structure with a double or triple bond between carbons. For example, the structure of R is illustrated in (a)-(m) below. R is preferably shown in (a).

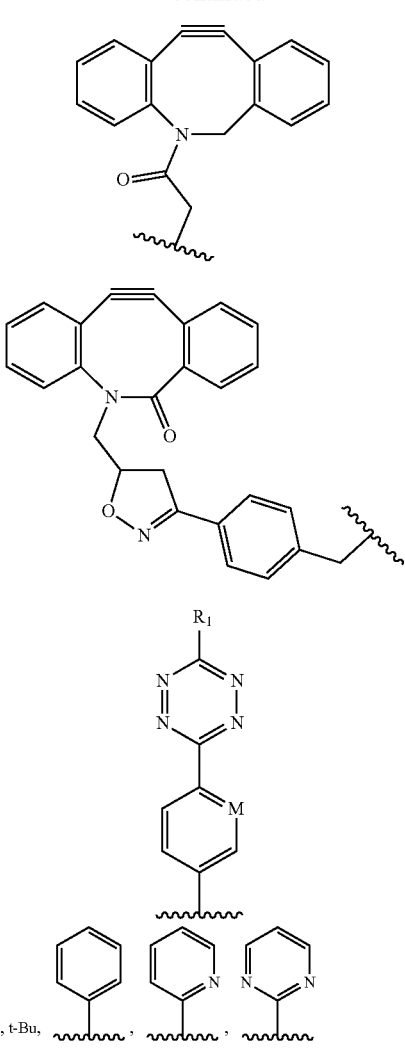

The monosaccharide derivatives of the present disclosure can be synthesized by a known method based on the structure from the monosaccharide as a starting material. For example, the monosaccharide derivative represented by Formula (I) can be synthesized by coupling with compound containing group R and the amino group of mannosamine hydrochloride. The resulting mannosamine derivative can be acetylated. Similarly, for the monosaccharide derivative represented by Formula (II), a compound containing group R is reacted with the amino group of glucosamine hydrochloride and the resulting glucosamine derivative can be acetylated. The structures of the synthesized monosaccharide derivatives can be confirmed by conventional methods such as nuclear magnetic resonance (NMR) and mass spectrometry (MS).

The cell labeling agent of the present disclosure can include only the monosaccharide derivative described above, or further contain the above monosaccharide derivative as an active ingredient and a pharmacologically acceptable carrier. The pharmacologically acceptable carriers are various organic or inorganic carrier materials used as formulation materials. The cell labeling agent can include, for examples, excipients, lubricants, binders, disintegrants, solvents, lysis aids, suspension agents, isotonic agents and buffers. The cell labeling agent also includes additives such as preservatives, antioxidants, colorants, sweeteners, etc., as necessary. The form of the cell labeling agent is not particularly limited, and examples thereof include solutions, granules, tablets and capsules.

When the cell labeling agent is a mixture of a monosaccharide derivative and other components, the monosaccharide derivative and the other components can be blended and formulated in a known manner. The content of the monosaccharide derivative in the cell labeling agent is not particularly limited; for examples, the cell labeling agent contains 1-100% by weight, 5-95% by weight, 10-90% by weight, 20-80% by weight, 30-70% by weight or 40-60% by weight of the monosaccharide derivative.

As described above, the monosaccharide derivatives are metabolized by the sialic acid biosynthetic pathway, which results in R being presented to the cell surface. Thus, the cell can be labeled by the cell labeling agent of the present disclosure. R is highly reactive because it is a group containing a ring structure with a double or triple bond between carbons. Because R is a structure that does not exist in the living body, it can be subjected to bioorthogonal reactions such as click reaction between R and tetrazine or azide or the like. This allows various functional substances to be specifically added to the sugar chains on the cell surface via R.

Next, the method for using the cell labeling agent in the present disclosure is described. To label cells by the above cell labeling agent, the cell labeling agent can be added to the cell medium and the cells can be exposed to the cell labeling agent. The concentration of cell labeling agent (monosaccharide) added to the medium is, for examples, 0.1 to 1 mM, 0.1 to 500 µM, 0.1 to 50 µM, 0.1 to 30 µM, or 1 to 25 µM.

The time for exposing the cells to the cell labeling agent is 12 to 96 hours or 48 to 96 hours, preferably 72 hours, depending on the cell type and the activity of the sialic acid biosynthetic pathway in the cells. After exposure to the cell labeling agent, the monosaccharide derivatives in the medium can be removed by washing cells. In this way, the cells can be labeled by the presented R on the cell surface.

For example, cells labeled with R can be visualized. To visualize the cells, a reporter substance that reacts with R can be used. The reporter substances include, for examples, fluorescent and luminescent substance bound to tetrazine or azide. Fluorescent substances include FAM, cyanine dyes, Cy3, Cy5, pyrene and rhodamine etc. By exposing the R-labeled cells to a reporter substance with a fluorescent material and a tetrazine group, the tetrazine can react with R and the fluorescent substance is added to the cell surface. The reporter substance can also be reacted with the lysate obtained by lysing the cells labeled with R.

When a fluorescent substance is used as a reporter substance, cells can be observed by a fluorescent image. Depending on the type of the reporter substance, fluorescence microscopy, fluorescence endoscopy, confocal endoscopy, multiphoton excitation fluorescence microscopy, narrow-band light observation, and confocal interference tomographic imaging observation can be used as observation methods.

The cell labeling agent of the present disclosure can label cells not only in vitro but also in vivo. When labeling cells in vivo, the cell labeling agent can be administered to the subject. The cell labeling agent can be administered to animals, such as zebrafish, killifish, frogs, mice, rats, dogs, rabbits, chimpanzees, monkeys, and humans.

The administration route of the cell labeling agent is not particularly limited. The cell labeling agent can be administered orally or parenterally, and may be administered systemically or locally. When administered to humans, the cell labeled agent can be administered by injection, catheter injection, spray, or smear to intravascular, sublingual, intrarectal, intraabdominal, skin, subcutaneous, intradermal, intra-bladder, tracheal, eye, nose, ear, etc.

The dose of cell labeling agent is not particularly limited as long as it is sufficient to label the targeted cells. When the cell labeling agent is administered to an animal, the dosage form, route of administration, and dose are appropriately selected depending on the weight or condition of the target animal. The dose of the cell labeling agent is also adjusted according to the types of cells and reporter substances. When administered to humans, the dosage range is, for examples, 0.01 to 1000 mg/kg, 0.1 to 100 mg/kg or 1 to 10 mg/kg per dose.

To visualize or detect R-labeled cells in an animal that administered by a cell labeling agent, such as a mouse, the target cells can be collected from the mouse and are exposed to a reporter substance as described above. If R is added to the cell surface, cells can be visualized or detected by the reporter substance. To facilitate observation, the cells can be fixed. Observation of a tissue section, prepared by a known method from the tissue of mice or the like administered with a cell labeling agent, can be performed by exposing to the reporter substance.

As described in detail above, according to the cell labeling agent of the present disclosure, a functional substance such as a reporter substance can be added to the cell surface without using a copper catalyst, since R is highly reactive. Therefore, the cell labeling agent administered into a living organism is highly safe and can be widely applied to clinical practice.

When R is included in the group attached to the 6-position of the sialic acid represented by Formula (III), R is not limited to the end group attached to the 6-position as the group attached to the carbon at the 9-position, the group attached to the carbon at 7 or 8-position can be included. If the monosaccharide derivative is a sialic acid represented by Formula (III), it is transported into the nucleus and presented to the cell surface without undergoing by the reactions A-D shown in FIG. 1. Therefore, the monosaccharide derivative represented by Formula (III) is presented to the cell surface earlier than the mannosamine and glucosamine derivatives, thus the cell can be labeled with higher efficiency.

When the monosaccharide derivative is a sialic acid represented by Formula (III), R can be included in the group substituted with the carboxyl group attached to the 2-position, and attached to the 4 or 5-position. R is preferably included in the group attached to the 5 or 9-position for efficient react with a reporter substance.

When the monosaccharide derivative is a sialic acid represented by Formula (IV), among the groups bonded to the carbon atoms constituting the six-membered ring, R can be included a group that does not change even if it is metabolized by the sialic acid biosynthetic pathway. Even with the monosaccharide derivative, cells can be labeled efficiently as in the case of the monosaccharide derivative represented by the Formula (III).

The cell labeling agent of the present disclosure is also useful for capturing sugar chains of cell surface or cells. When capturing cells, for example, biotin can be bound to R using a click reaction. Cells with biotin on the surface can be captured by, for example, a column with streptavidin immobilized on a carrier. The cell labeling agent is also useful for detection or quantification of sugar chains, when R is added to the sugar chains on the cell surface.

The reporter substance can also include a radionuclide. By adding radionuclides to the cell surface, cells can be detected or visualized by autoradiography, positron emission tomography (PET) or computed tomography projection (SPECT). The radionuclide is not particularly limited and is selected according to the mode of use.

For example, for the detection of cells by PET, a positron-emitting radionuclide such as $^{11}C$, $^{14}C$, $^{13}N$, $^{15}O$, $^{18}F$, $^{19}F$, $^{62}Cu$, $^{68}Ga$ and $^{78}Br$ can be used. For the detection of cells by SPECT, nuclides emitting γ rays such as $^{99m}Tc$, $^{111}In$, $^{67}Ga$, $^{201}Tl$, $^{123}I$ and $^{133}Xe$ can be used.

A functional group and other groups such as a free radical can be also added to the cell surface via R. If a functional group with a free radical is added to the surface of a cancer cell, the free radicals inhibit the growth of cancer cells.

In addition to azide and tetrazine, cyclooctyne, cyclooctene, cyclobutene and cyclopropene can be used as reporter substances to react with R.

In other embodiments, a cell labeling kit can be provided. The cell labeling kit includes the cell labeling agent of the present disclosure and a reporter substance that binds to the sialic acid by reacting with the group, that is R, presented outside the cell, wherein the group is not changed when metabolized by the sialic acid biosynthetic pathway.

There is provided a method of disease diagnosis using a cell labeling agent according to the present embodiment. The diagnostic method includes a first administration step by administering the cell labeling agent to the subject, a second administration step by administering a reporter substance that reacts with R and binds to the sialic acid to the subject, and an evaluation step by detecting or quantifying a reporter substance.

The diagnostic method can preferably be used to diagnose cancer and inflammation or the like. In cancer and inflammatory cells, the sialic acid biosynthetic pathway is activated and more sialic acid is presented to the cell surface in comparison to normal cells. Thus, for example, cancer and inflammation or the like can be diagnosed by comparing the amount of a reporter substance from a normal tissue of a subject or a cell of healthy person. The cell labeling agent can rapidly add a reporter substance or the like to the surface of cells, and thus can quickly diagnose.

EXAMPLES

The following examples describe the present disclosure in detail, but the present disclosure is not limited by the examples.

Example 1

Synthesis of Monosaccharide Derivative
BCN-ManNAc 35.9 mg of D-mannosamine hydrochloride was placed in a flask, and nitrogen replacement were repeated three times. The inside of the reaction system was replaced with nitrogen. 2 mL of dehydrated DMF (dimethylformamide), 53.3 mg of (1R,8S,9s)-bicyclo[6.1.0]non-4-yn-9-ylmethyl N-succinimidyl carbonate (BCN-NHS) and 58 µL of N,N-diisopropyl ethylamine (DIEA) were added, and the mixture was stirred at room temperature for 12 hours. After the reaction, the solvent was removed by an evaporator, followed by silica column chromatography (dichloromethane: methanol=4:1) for purification. Fractions containing the desired product were collected in a flask, the solvent was removed by an evaporator, and dried by a vacuum pump. As a result, 42.2 mg of BCN-modified mannosamine (BCN-Man) was obtained in 71% yield.

35.0 mg of BCN-Man was placed in a flask and the reaction system was replaced with nitrogen. Then 1 mL of dehydrated pyridine and 93 μL of acetic anhydride were added and stirred for 5 hours at room temperature. After the reaction, the solvent was removed by an evaporator, followed by silica column chromatography (hexane:ethyl acetate=1:1) for purification. Fractions containing the desired product, acetylated BCN-modified mannosamine (BCN-ManNAc), were collected in a flask, the solvent was removed by an evaporator, and the fraction was dried by a vacuum pump.

Results

Figure 2:
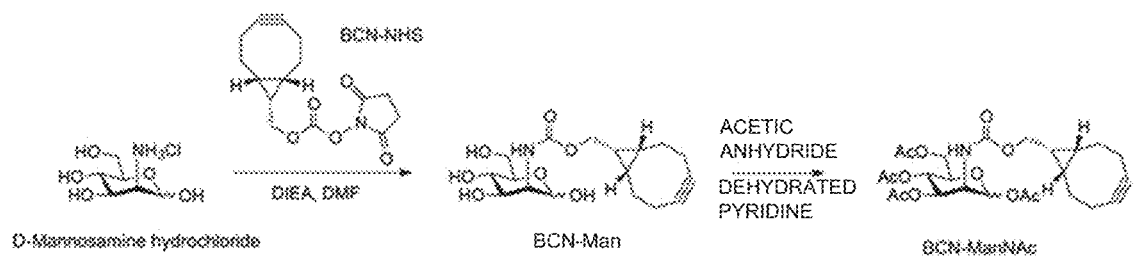
FIG. 2 shows the synthetic scheme of a monosaccharide derivative according to Example 1 of the present disclosure.

The structures of D-mannosamine hydrochloride, BCN-Man and BCN-ManNAc are shown in FIG. 2. As a result, 27.2 mg of BCN-ManNAc was obtained in 53% yield. The structure of BCN-ManNAc was identified by NMR (AV-400M, Bruker) and MS (Exactive, Thermo Fisher) as shown in below.

$^1$H-NMR (CDCl$_3$) δ: 6.09 (s, 1H), 5.30 (dd, J=4.2, 10.2 Hz, 1H), 5.21-5.00 (m, 3H), 4.48-4.01 (m, 4H), 2.30-2.23 (m, 4H), 2.17 (s, 3H), 2.11-2.02 (m, 4H), 2.10 (s, 3H), 2.05 (s, 3H), 2.01 (s, 3H), 1.57 (m, 1H), 1.39 (m, 1H), 0.97 (m, 1H).

$^{13}$C-NMR (CDCl$_3$) δ: 170.61, 170.07, 169.65, 168.18, 156.11, 98.75, 91.88, 73.39, 71.53, 70.19, 69.15, 65.33, 63.65, 61.97, 51.11, 29.01, 21.39, 20.89, 20.75, 20.64, 20.19, 17.62.

ESI-MS (M+Cl)$^-$ for $C_{25}H_{33}O_{11}NCl$. Calculated: 558.1737; Found: 558.1806.

Example 2

Confirmation of the Reactivity of BCN-ManNAc In Vitro 2.0 mg of BCN-ManNAc was dissolved in 190 μL of DMSO and 20 mM of BCN-ManNAc solution was prepared. 1.0 mg of FAM-tetrazine was dissolved in 180 μL of DMSO and 10 mM of FAM-tetrazine solution was prepared. 89 μL of phosphate-buffered saline (PBS) was prepared in a microtube, to which 1 μL of BCN-ManNAc solution and 10 μL of FAM-tetrazine solution were added, and the mixture was stirred well in a vortex mixer. The final concentrations of BCN-ManNAc and FAM-tetrazine in the mixture are 200 μM and 1 μM, respectively.

100 μL of the mixture was reacted at 37° C. for 1.5 hours. As a control, 100 μL of the sample of BCN-ManNAc 200 μM only was prepared. The fluorescence spectra of the mixture and control were measured using a spectrophotometer (JASCO FP-8200) (λex=492 nm, λem=517 nm). To evaluate the time dependence of the reaction of BCN-ManNAc and FAM-tetrazine, the fluorescence spectra of 100 μL of the mixture were measured up to 4000 s in the time-varying measurement mode.

Results

Figure 3:
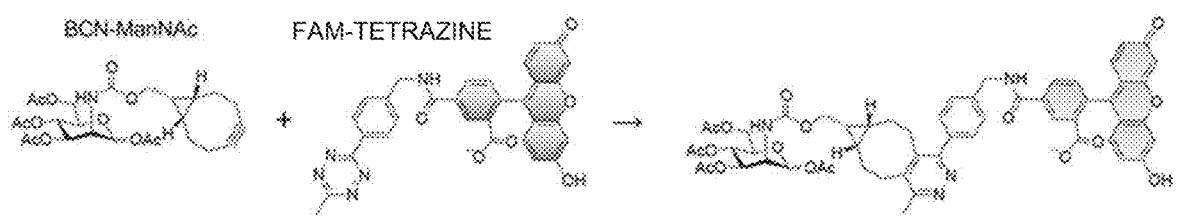
FIG. 3 shows the click reaction between the monosaccharide derivative and a reporter substance, including a fluorescent dye in Example 1.
Figure 4:
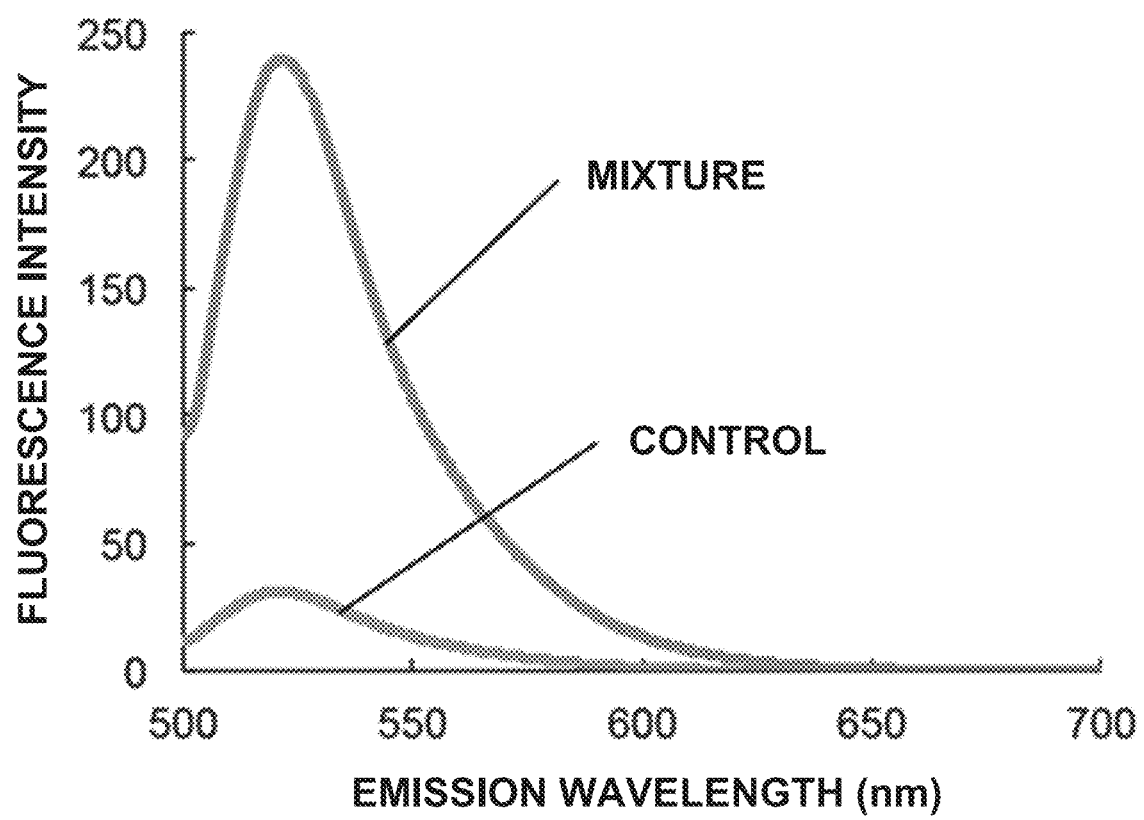
FIG. 4 shows the fluorescent spectrum of a fluorescent dye bound to the monosaccharide derivative in Example 1.
Figure 5:
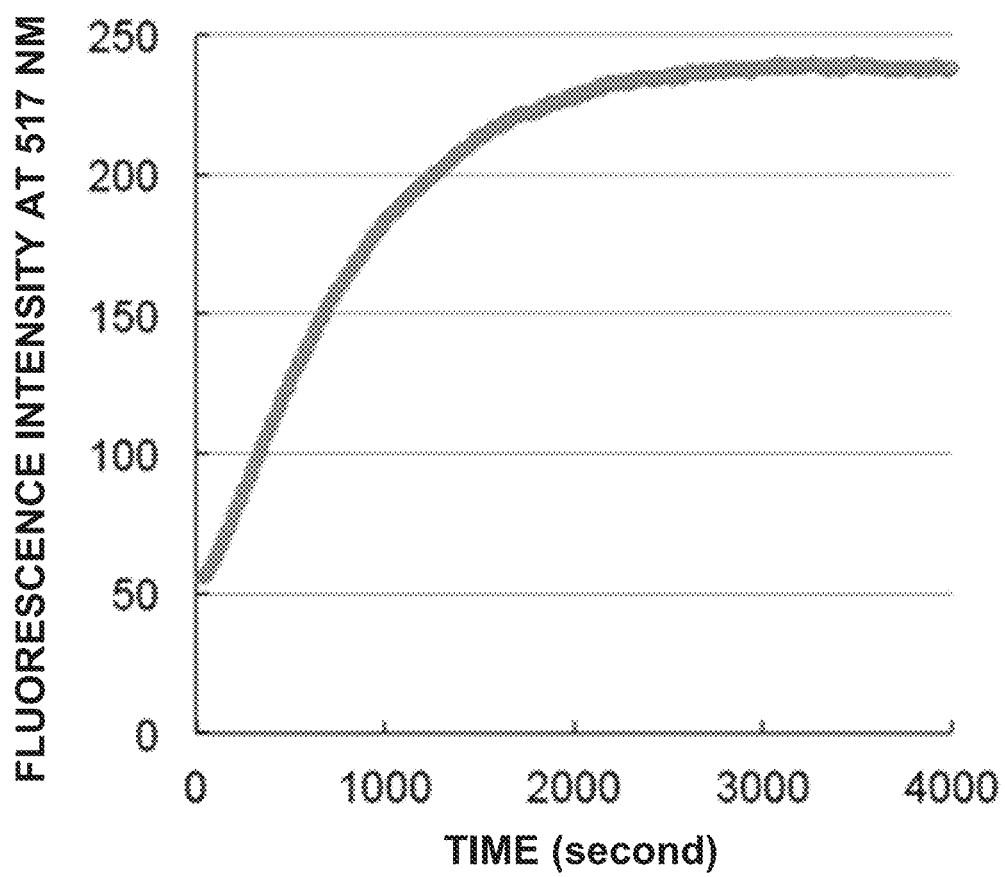
FIG. 5 shows the time course of the fluorescence signal of a fluorescent dye bound to the monosaccharide derivative in Example 1.

As shown in FIG. 3, when FAM-tetrazine binds to BCN-ManNAc, FAM fluorescence is strongly emitted. FIG. 4 shows the fluorescence spectra of the mixture and control. When BCN-ManNAc reacted with FAM-tetrazine, the fluorescence intensity was shown to increase significantly. FIG. 5 shows the changes in the fluorescence spectrum of the mixture over time. It was shown that the fluorescence intensity almost reached its maximum after about 1800 s.

Example 3

Fluorescence Imaging of Cells

BCN-ManNAc was added to the medium containing 1×10$^5$ HeLa cells and cultured for 72 hours. The medium used was DMEM (Dulbecco's Modified Eagle's Medium) containing 10% FBS (fetal bovine serum). The final concentrations of BCN-ManNAc added to the medium were 0, 2.5, 5, 10, 20, and 25 μM. After incubation, the medium was removed and the cells were washed three times with PBS. 3.7% paraformaldehyde was added and the cells were fixed for 20 min at room temperature. A final concentration of 1 μM FAM-tetrazine was added to the plate containing the fixed cells, and the cells were incubated for 20 min at room temperature. Fluorescence measurement was performed using a confocal microscopy (Leica TCS SP8, Leica Microsystems).

Results

Figure 6:
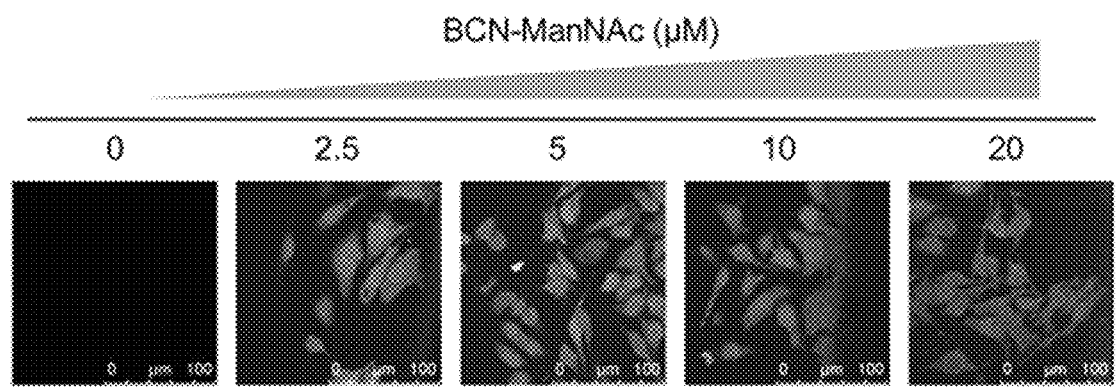
FIG. 6 shows the fluorescent images of HeLa cells by the monosaccharide derivative and fluorescent substance in Example 1.
Figure 7:
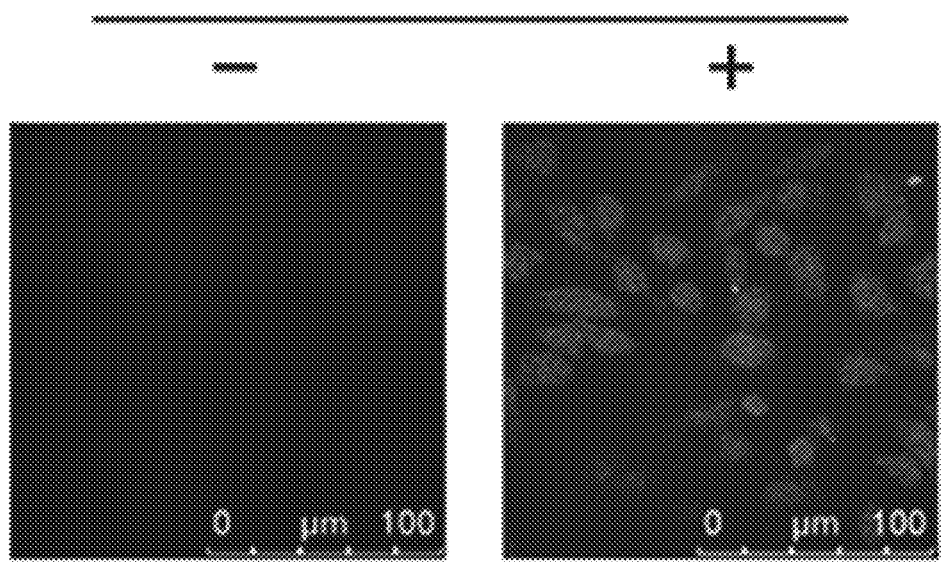
FIG. 7 shows the fluorescent images of HeLa cells cultured in media containing a monosaccharide derivative at a concentration of 25 μM in Example 1, stained with (+) or without (−) FAM-tetrazine.

FIG. 6 shows fluorescence images of cells by confocal microscopy. The fluorescence of FAMs bound to BCN-ManNAc was observed. The fluorescence of FAM was not observed in cells cultured in medium without BCN-ManNAc, but increased in a concentration-dependent manner with BCN-ManNAc. FIG. 7 shows fluorescence images of cells cultured in medium containing 25 μM BCN-ManNAc. Cells exposed to FAM-tetrazine (+) were observed by fluorescence, whereas cells not exposed to FAM-tetrazine (−) were not observed. These results indicated that cells cultured in medium containing BCN-ManNAc could be visualized by exposure to FAM-tetrazine.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2018-18172, filed on Feb. 5, 2018, the entire disclosure of which is incorporated by reference herein.

INDUSTRIAL APPLICABILITY

The present disclosure is suitable for cell labeling and diagnosis of cancer and inflammation.

The invention claimed is:

1. A cell labeling agent, comprising a compound of Formula (I),

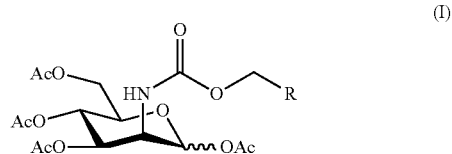

wherein R is
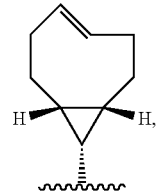 , 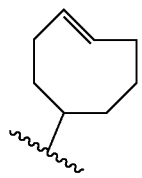 , 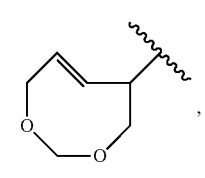 ,
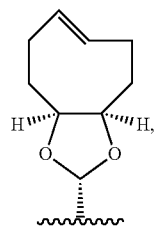 , 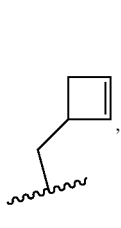 , 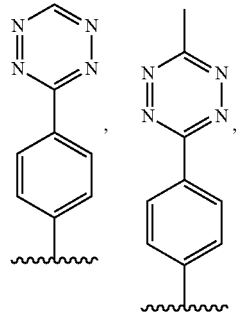 ,
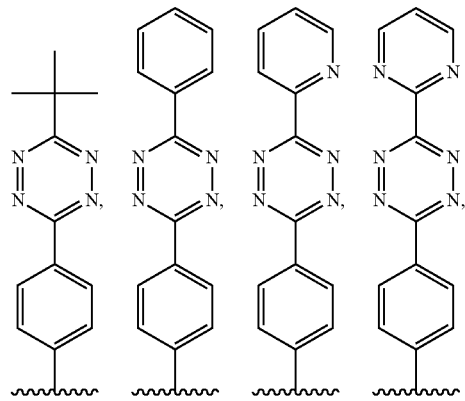 ,
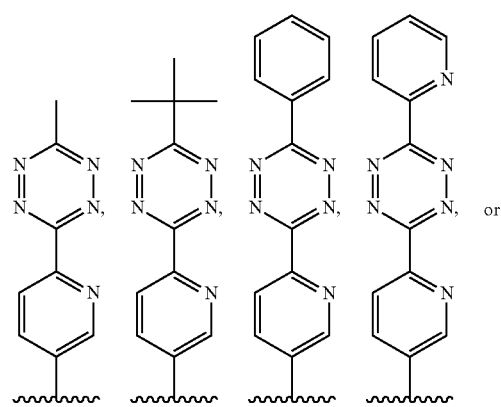 or
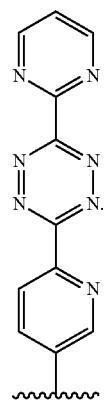
2. A cell labeling agent, comprising a compound of Formula (II),
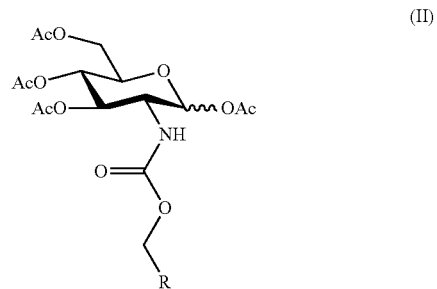 (II)
wherein R is
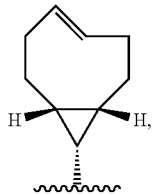 , 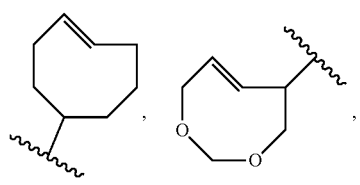 ,
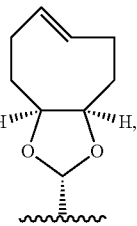 , 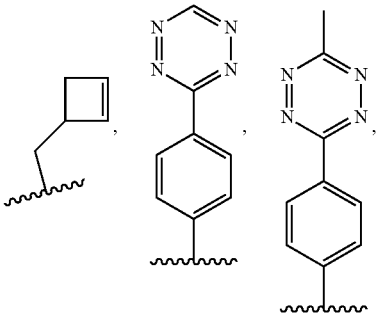

-continued
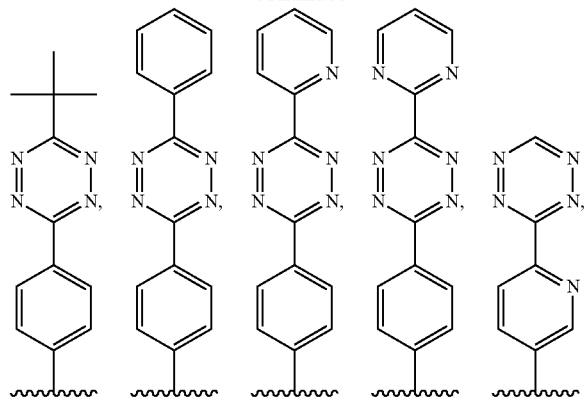
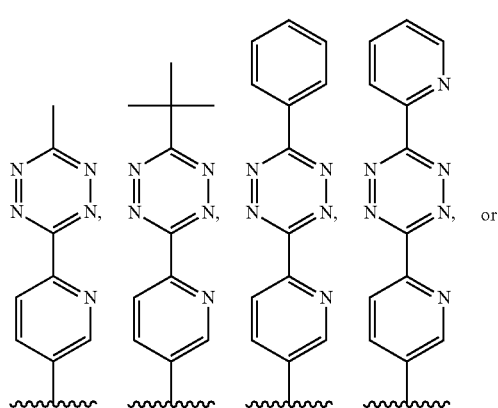
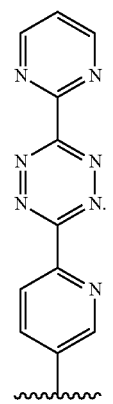
3. A cell labeling agent, comprising a compound of Formula (III),
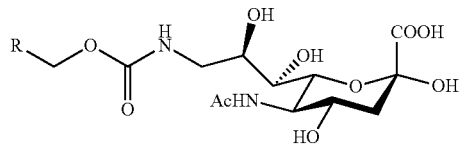
(III)
wherein R is
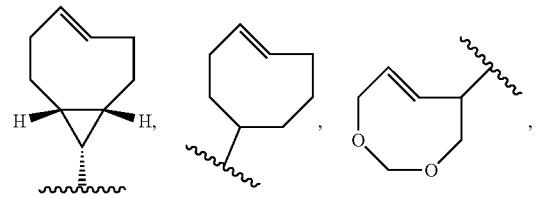
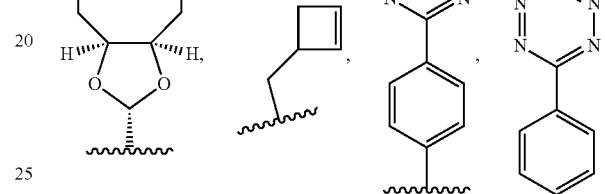
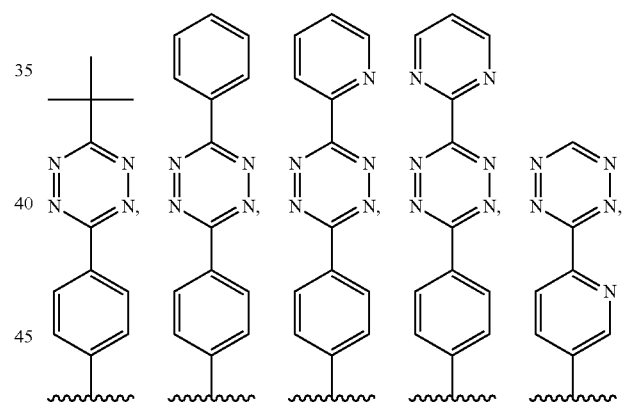
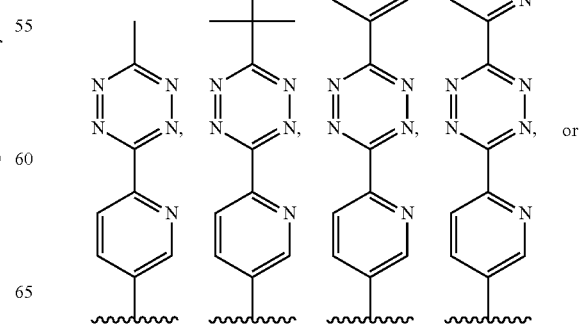

-continued

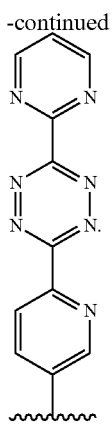

4. A cell labeling kit, comprising the cell labelling agent of claim 1, and a fluorescent or luminescent reporter substance.

5. The cell labelling kit of claim 4, wherein the fluorescent or luminescent reporter substance is bound to a tetrazine or an azide.

6. The cell labelling kit of claim 4, wherein the fluorescent or luminescent substance includes FAM, a cyanine dye, a pyrene, or a rhodamine.

7. The cell labelling kit of claim 4, wherein the fluorescent or luminescent substance includes Cy3 or Cy5.

8. A cell labeling kit, comprising the cell labelling agent of claim 2, and a fluorescent or luminescent reporter substance.

9. The cell labelling kit of claim 8, wherein the fluorescent or luminescent reporter substance is bound to a tetrazine or an azide.

10. The cell labelling kit of claim 8, wherein the fluorescent or luminescent substance includes FAM, a cyanine dye, a pyrene, or a rhodamine.

11. The cell labelling kit of claim 8, wherein the fluorescent or luminescent substance includes Cy3 or Cy5.

12. A cell labeling kit, comprising the cell labelling agent of claim 3, and a fluorescent or luminescent reporter substance.

13. The cell labelling kit of claim 12, wherein the fluorescent or luminescent reporter substance is bound to a tetrazine or an azide.

14. The cell labelling kit of claim 12, wherein the fluorescent or luminescent substance includes FAM, a cyanine dye, a pyrene, or a rhodamine.

15. The cell labelling kit of claim 12, wherein the fluorescent or luminescent substance includes Cy3 or Cy5.

* * * * *